United States Patent [19]

Palti

[11] 4,353,523

[45] Oct. 12, 1982

[54] FLOW REGULATOR

[76] Inventor: Yoram Palti, 49 Ruth St., Haifa, Israel

[21] Appl. No.: 74,301

[22] Filed: Sep. 11, 1979

[30] Foreign Application Priority Data

Sep. 13, 1978 [DE] Fed. Rep. of Germany ....... 2839774

[51] Int. Cl.³ ............................................. F16K 31/08
[52] U.S. Cl. ...................................... 251/65; 116/277;
128/214 C; 137/556; 137/433; 251/133;
335/306
[58] Field of Search ................. 251/65, 133, 134, 129;
335/302, 306; 128/214 C, 214 R, 214.2, 214 F,
DIG. 12; 137/556, 433; 116/204, 277

[56] References Cited

U.S. PATENT DOCUMENTS

| | | | |
|---|---|---|---|
| 2,289,574 | 7/1942 | Carlson | 251/65 |
| 2,346,904 | 4/1944 | Carlson | 251/65 |
| 2,536,813 | 1/1951 | Jones et al. | 251/65 |
| 2,589,188 | 3/1952 | DeCraene et al. | 251/65 |
| 2,644,477 | 7/1953 | King | 251/65 |
| 2,700,395 | 1/1955 | Young | 251/65 |
| 2,792,194 | 5/1957 | Huck | 251/65 |
| 2,869,563 | 1/1959 | Schoengrun | 251/65 |
| 3,223,898 | 12/1965 | Bey | 335/306 |
| 3,287,676 | 11/1966 | Davis et al. | 335/306 |
| 3,347,262 | 10/1967 | Gibson | 137/375 |
| 3,348,543 | 10/1967 | Stafford | 128/214 R |
| 3,355,140 | 11/1967 | Andersen | 251/65 |
| 3,747,892 | 7/1973 | Gigantino | 251/366 |
| 3,774,878 | 11/1973 | Martinez | 251/250 |

FOREIGN PATENT DOCUMENTS

| | | | |
|---|---|---|---|
| 87017 | 3/1952 | Denmark | 335/306 |
| 1091084 | 4/1955 | France | 336/306 |
| 185296 | 10/1963 | Sweden | 335/306 |
| 642353 | 8/1950 | United Kingdom | 335/306 |
| 697051 | 9/1953 | United Kingdom | 335/306 |
| 899634 | 6/1962 | United Kingdom | 335/306 |

Primary Examiner—George L. Walton
Attorney, Agent, or Firm—Hubbell, Cohen, Stiefel & Gross

[57] ABSTRACT

A device for the regulation of the flow area of a valve having an inner magnet (32) moveably mounted on a valve plug (22) to move the valve plug (22) in an axial direction, and an outer magnet (28) moveably mounted to the valve housing to move the inner magnet (32) and consequently the valve plug (22) as the outer magnet (36) is moved.

10 Claims, 4 Drawing Figures

FLOW REGULATOR

TECHNICAL FIELD

The invention relates to a device for regulating the flow area of a valve for gases or liquids, particularly to a valve attached to a device for intravenous infusion of fluids, a valve housing, a valve opening, and a valve ram (knocker) cooperating therewith.

BACKGROUND ART

Devices for regulating the flow of a liquid are known. German Offenlegungsschrift No. 26 44 140, for example, shows the cross-section of a valve opening which is regulated with a needle-valve axially moveable by a thread. The corresponding thread bolt extends through the housing to the outside and is manually actuated.

Disadvantages have been experienced in the use of devices of the prior art. The use of seals allows germs to migrate along the thread from the outside to the inside which, during the use for intravenous infusion, may lead to an infection of the patient. Moreover, air may enter along the thread of the needle valve which may result in great danger to the patient if an air bubble enters a vein.

DISCLOSURE OF THE INVENTION

An object of the present invention is, therefore, to eliminate the above disadvantages and to provide a device which will regulate the flow without contacting the flow area of the valve.

According to the present invention at least one magnet is moveably mounted outside the valve housing and at least one magnet is mounted within the valve housing on the valve plug and is moveable with the plug in the axial direction of the valve plug. The movement of the magnet mounted on the outside of the valve housing moves the magnet on the inside and consequently the valve plug.

The inner magnet, preferably a permanent magnet, may be mounted at the end of the shaft of the valve plug opposite of the valve opening.

Preferably, the inner permanent magnet is of a ring-shaped or annular form and is formed by several circumferentially spaced segments resulting in channels between segments to permit the flow of liquid. In order to ease the flow, the segments may be tapered in the direction of the valve opening.

The valve housing is surrounded by the outer magnet which is rotatably mounted around the axis of the valve housing. Preferably, the outer magnet has a plurality of circumferentially distributed magnets. The inner magnet has the same number of circumferentially distributed magnets as the outer magnet. The magnets are arranged so that the inner magnets are poled oppositely to the outer magnets. Suitably, all inner magnets have one polarity at their ends adjacent to the outer magnet, while all outer magnets have the opposite polarity to the inner magnet.

Alternatively, the outer magnet consists of an even number of magnets having alternating polarity. The inner magnet consists of half the number of magnets as in the outer magnet. The polarity of the inner magnets are the same on their ends adjacent to the outer magnet and the inner magnets are angularly spaced twice the angular distance as the outer magnets.

Preferably, within the area of the inner magnets mounted to the valve plug, the housing is provided with an internal thread and the magnet is provided with an external thread for engagement therewith, so that when the outer magnet is turned, the inner magnet is also turned which, through the engaging threads, results in the valve plug moving axially.

To decrease friction one of the threads is continuous and the other is formed of short segments.

The inner magnet may be provided with an indicator and the housing with a corresponding scale, in order to regulate and check the movement of the inner magnet axially and circumferentially direction.

BRIEF DESCRIPTION OF THE DRAWINGS

The following description of the preferred embodiment is made with reference to the accompanying drawings, is exemplary only and is not intended to limit the scope of the invention.

BEST MODE FOR CARRYING OUT THE INVENTION

Figure 1:
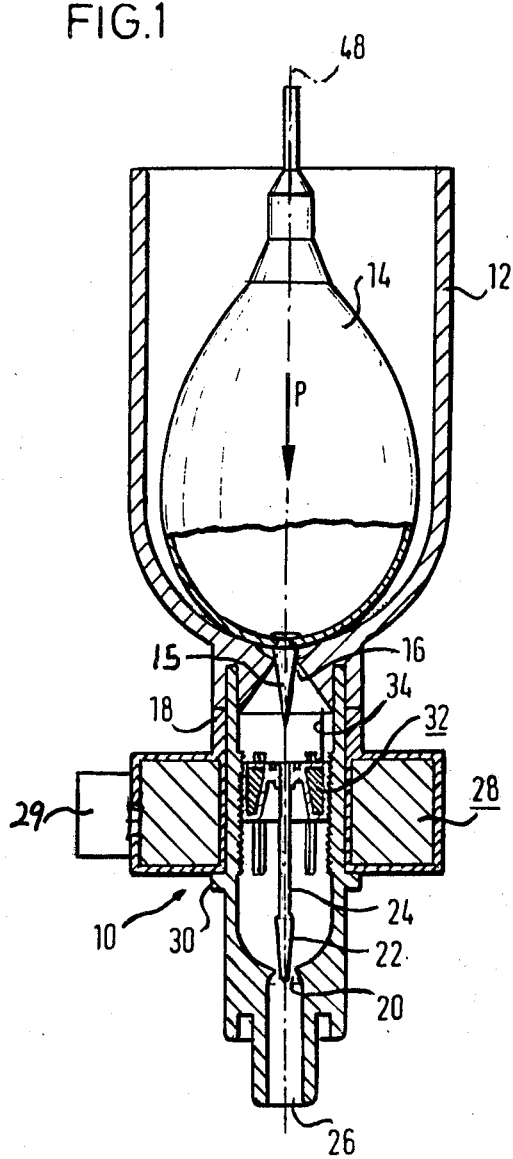
FIG. 1 is a longitudinal cross-sectional view of my device for regulating the flow area.

FIG. 1 shows the device of the present invention in combination with a device for intravenous infusion having a float housing 12 in which is disposed a float 14 with a tapered end 15 depending therefrom to more or less open or close an opening 16 located between the float housing 12 and the valve housing 18 of the device 10.

Located within the valve housing 18 is a valve opening 20 cooperating with a tapered valve plug 22 moveable in the axial direction, i.e., along the longitudinal axis or center axis 48 of the entire device, for more or less opening or closing of the valve opening 20.

Communicating with the valve opening 20 is a supply channel 26, suitable for attaching a hose (not shown) thereto.

The valve plug 22 is provided with a shaft 24 having at its end away from the valve opening 20 a permanent magnet 32. A ring-shaped magnet 28 sitting on an annular collar 30 of the valve housing 18. The magnet 28 is located on the outside of valve housing 18 and concentrically surrounding its center axis 48. The magnet 28 is mounted in any suitable manner for rotation around the center axis 48 without, however, being moveable in the axial direction.

The magnet 28, which may be a permanent magnet or a suitable electro-magnet, may be turned manually or mechanically, e.g., by a motor, particularly a stepping motor 29.

Figure 3:
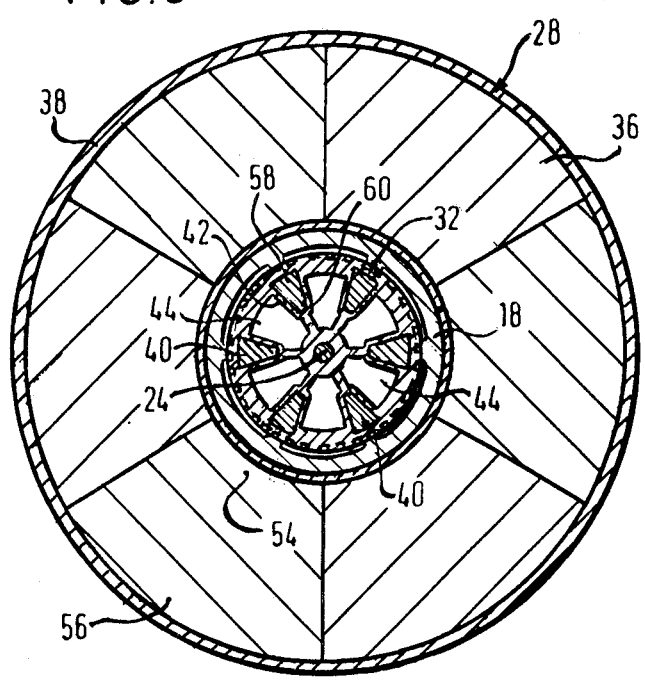
FIG. 3 shows a cross-sectional view taken through the line 3—3 in FIG. 2.

As shown in FIG. 3, the outer magnet 28 consists of several, in the example six single magnets 36. Preferably, the magnets 36 are uniformly and circumferentially distributed and surrounded by a magnet housing 38. The single magnets 36 are arranged such that, for example, the south poles of all single magnets 36 are facing the inner end 54 and the north poles of all single magnets 36 are facing the outer end 56 or vice versa. In the depicted embodiments, the single magnets 36 are formed in abutting segments. The single magnets, however, may also have a spaced arrangement whereby the single magnets are suitably arranged at the same angular distances.

As is shown in FIG. 3, the inner magnet 32 is also formed by several single magnets 40 located in a magnet housing 42. The single segments or single magnets 40 are also preferably uniformly circumferentially distributed and spaced apart by channels 44 for the passage of the liquid or gas flowing through the device in the axial direction indicated by arrow P in FIG. 1.

The number of the single magnets 40 of the inner magnet 32 is preferably equal to the number of single magnets 36 of the outer magnet 28. The polarity of each inner single magnet 40 is opposite to the polarity of the outer magnets, e.g., when the south poles of the outer single magnets 36 are facing the inner end 54, the north poles of all inner single magnets 40 are facing the outer end 58, while the south poles of the inner single magnets 40 are facing the inner end 60. Consequently, in each pair of magnets, consisting of one outer single magnet 36 and one inner single magnet 40, the two poles of opposite polarity are facing each other.

Figure 4:
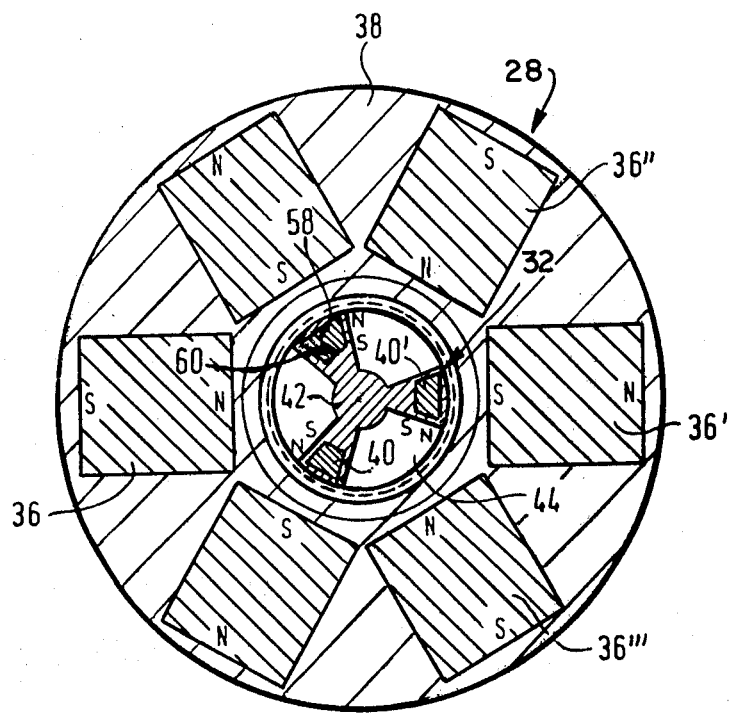
FIG. 4 shows a view similar to FIG. 3 of a second embodiment for the inner and outer magnets.

In the embodiment according of FIG. 4, the outer magnet 28 also consists six single magnets 36.

As is shown in FIG. 4, however, the polarity of the single magnets 36 alternates in a circumferential direction. In FIG. 4, the number of the outer single magnets 36 is even. The inner magnet 32 is also formed of segments or single magnets 40 built in a magnet housing 42. However, the number of single magnets 40 in the embodiment shown in FIG. 4, is half of the number of the outer magnets 36. The outer magnets 36, for example (with six single magnets), are arranged at angular distances of 60°, while the single magnets 40 of the ring-shaped inner magnet 32 are arranged at angular distances of 120°. Flow channels 44, for the free flow of the corresponding fluid, are formed between the inner magnets 40.

The inner single magnets 40 are also arranged in such a way that all single magnets 40 are facing such that their homologous poles 58 are all facing outside and their opposite homologous poles 60 are facing inside. In the embodiment shown, each single magnet 40 has the north pole at its outside 58 and the south pole at its inside 60. The reverse arrangement is, of course, also possible.

As shown, the south pole of each second outer single magnet 36 is facing the north pole of an inner single magnet 40. The north pole of each inner single magnet 40 is thus attracted by the south pole of the radially opposite outer single magnet 36, while being repelled by the two north poles of the single magnets 36 adjacent to the first mentioned single magnet.

Figure 2:
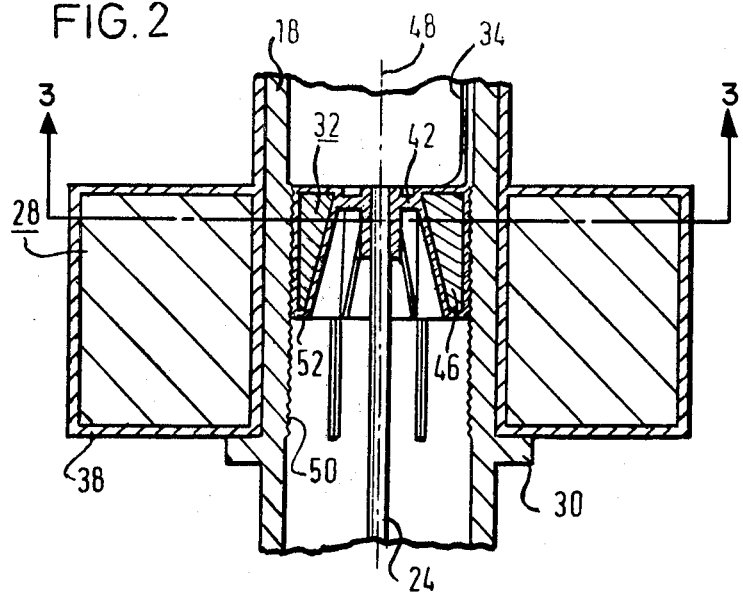
FIG. 2 is a fragmentary longitudinal sectional view in enlarged scale of the arrangement of inner and outer magnets in my device.

As is particularly shown in FIG. 2, the valve housing 18 is provided at its inner wall with an internal thread 50 while the inner magnet 32 is provided on its outer wall with an external thread 52 engaging with the internal thread 50, so that by turning the outer magnet, the inner magnet 32 will turn and this will translate into axial movement in the direction of axis 48. In order to reduce the friction between the engaging threads, one of the two threads, i.e., either the internal thread 50 or the external thread 52 may be continuous, while the other thread is preferably formed in several short segments to reduce sliding friction. Of course, both threads can be continuous.

The device of the invention operates as follows:

The desired adjustment of the flow area of the valve opening 20 is achieved by axial movement of the valve plug 22, whereby in one final position the valve opening 20 is completely open and in another second final position the opening is completely closed. Due to the conical shape of the valve plug 22 any desired position for the cross-section of the flow-opening is possible, depending on the axial position of the valve plug 22.

Starting at any given position, when the outer magnet 28, which may be formed of two halves and connected to each other by joints, is turned around the axis 48, the inner magnet 32, which is easily moveable within internal thread 50, is also rotated because of the magnetic attraction between pairs of magnets 36 and 40 and through the action of interfitting threads 50 and 52 is thus axially moved.

In the embodiment shown in FIG. 3, each south pole of an inner single magnet 40 is facing a north pole of an outer single magnet 36 so that the rotational movement of the outer magnet, due to the attractive power between each pair of magnets, is transmitted to the inner magnet.

In the embodiment shown in FIG. 4, the south pole of the outer single magnet 36' is facing the north pole of single inner magnet 40'. Thus, while turning the outer ring-shaped magnet 28, due to the attractive power between the south pole of single magnet 36' and the north pole of single magnet 40', a torsional moment is exercised on the inner magnet 32 which is put into motion, since this torsional moment is created at each of the three pairs of magnets, each consisting of one inner and one outer single magnet. According to the embodiment shown in FIG. 4, when the outer magnet 28 turns clockwise the north pole of the outer single magnet 36" is exercising a repelling power to the north pole of the inner single magnet 40' thus also creating a torsional moment. When turned counter-clockwise, the north pole of the single magnet 36" exercises a repelling power to the north pole of the inner single magnet 40'. These relations apply to all pairs of magnets.

As already mentioned, the segments or single magnets 40 of the inner permanent magnet 32 are tapered in the direction of the valve opening 20 (FIG. 1), as shown at 46 in FIG. 2. This arrangement prevents air bubbles, possibly pulled along with the fluid from the float housing 12, to be collected beneath magnet 32. Such air bubbles, should they ever be pulled along, may then ascend along the sloping surface of the tapered magnet segments.

As diagrammatically depicted in FIG. 2, the inner magnet 32 is provided with an indicator 34 in cooperative arrangement with a scale (not shown) on the valve housing 18 for enabling the indication and regulation of the axial position as well as circumferential position of the inner magnet 32 and thus the axial position of the valve ram 22 (FIG. 1). At least a part of the valve housing 18 is therefore suitably made of transparent material.

Thus, as is obvious from the foregoing description and drawings, the valve, formed by valve plug 22 and valve opening 20 is externally adjustable without the valve housing 18 having an opening for the passage of an actuating element for valve ram 22. The area of the valve plug and valve opening 20 is thus completely sealed relative to the outside and it is impossible for air bubbles or germs to migrate to the inside. Moreover, since the valve plug is arranged in and also moves in the flow direction of the fluid, turning of the fluid is not necessary so that the danger of possible inclusion of air bubbles as well as the formation of whirlpools is prevented.

When the outer ring-shaped magnet 28 is actuated by an electrical stepping motor 29, turning the outer magnet corresponding to a desired flow rate, the motor is suitably connected with a flow-meter, a drop-counter, or the like.

What is claimed is:

1. A device for regulating the flow area of a valve for fluids comprising:
    a valve housing having a fluid inlet and outlet and a valve opening;
    a valve plug for opening and closing said valve opening;
    an outer magnet rotatably mounted on the outside of said valve housing, said outer magnet comprising a plurality of alternately poled, circumferentially distributed magnet segments;
    an inner magnet comprising one or more magnet segments fixedly mounted on said valve plug within said valve housing, said inner magnet segments being mounted for rotatable and axial movement to move the valve plug in an axial direction when said outer magnet is moved, all of said inner magnet segments having the same pole confronting said outer magnet and being distributed for simultaneous alignment with the oppositely poled outer magnet segments to prevent the loss of magnetic flux to neighboring inner and outer magnet segments whereby the magnetic attraction between said inner and outer magnets is enhanced.

2. The device according to claim 1, wherein said outer magnet comprises an even number, four or greater, of outer magnet segments; and wherein said inner magnet comprises a plurality of inner magnet segments equal to half the number of outer magnet segments.

3. A device according to claim 2, wherein inner and outer magnet segments are arranged at equal angular distances.

4. A device according to claim 3, wherein said inner magnet segments are permanent magnets, and are mounted at the end of said valve plug opposite said valve opening.

5. A device according to claim 4, wherein said inner magnet segments are spaced apart to define channels therebetween for the flow of fluid.

6. A device according to claim 5, wherein said segments of the inner magnet are tapered in the direction of the valve opening.

7. A device according to claim 6, wherein the valve housing, within the area of the inner magnet, is provided with an internal thread and the inner magnet includes an external thread in engagement therewith, such that by turning the outer magnet, the inner magnet will also turn and the valve plug and inner magnet will move axially.

8. A device according to claim 7, wherein one of said threads is formed continuously and the other is formed of short segments.

9. A device according to claim 8, further comprising an indicator mounted at the inner magnet, and said valve housing provided with a scale for adjusting the axial and circumferential position of the inner magnet.

10. The device according to claim 1, wherein said valve opening is said fluid outlet.

* * * * *